United States Patent
Yotani et al.

(10) Patent No.: US 9,689,848 B2
(45) Date of Patent: Jun. 27, 2017

(54) COLUMN CONTAINED IN CONTAINER AND COLUMN CONTAINER

(71) Applicant: SEKISUI MEDICAL CO., LTD., Chuo-ku (JP)

(72) Inventors: Takuya Yotani, Chuo-ku (JP); Yuriko Nemoto, Chuo-ku (JP); Hideki Muraki, Fussa (JP)

(73) Assignee: SEKISUI MEDICAL CO., LTD., Chuo-ku (JP)

(*) Notice: Subject to any disclaimer, the term of this patent is extended or adjusted under 35 U.S.C. 154(b) by 0 days.

(21) Appl. No.: 15/026,175

(22) PCT Filed: Sep. 30, 2014

(86) PCT No.: PCT/JP2014/076053
§ 371 (c)(1),
(2) Date: Mar. 30, 2016

(87) PCT Pub. No.: WO2015/046566
PCT Pub. Date: Apr. 2, 2015

(65) Prior Publication Data
US 2016/0223501 A1 Aug. 4, 2016

(30) Foreign Application Priority Data
Sep. 30, 2013 (JP) ................................ 2013-203036

(51) Int. Cl.
*B01D 15/22* (2006.01)
*G01D 11/24* (2006.01)
(Continued)

(52) U.S. Cl.
CPC ..... *G01N 30/6047* (2013.01); *B65D 41/0407* (2013.01); *B65D 53/02* (2013.01); *G01N 30/6004* (2013.01)

(58) Field of Classification Search
CPC .............................. G01D 11/24; G01D 11/245
(Continued)

(56) References Cited

U.S. PATENT DOCUMENTS 3,763,879 A * 10/1973 Jaworek ............... B01L 3/5021
137/268
3,904,527 A 9/1975 Wilhelmson et al.
(Continued)

FOREIGN PATENT DOCUMENTS

CN 2400380 Y 10/2000
CN 2553381 Y 5/2003
(Continued)

OTHER PUBLICATIONS

International Search Report Issued Dec. 22, 2014, in PCT/JP2014/076053 Filed Sep. 30, 2014.
(Continued)

*Primary Examiner* — Lisa Caputo
*Assistant Examiner* — Jamel Williams
(74) *Attorney, Agent, or Firm* — Oblon, McClelland, Maier & Neustadt, L.L.P.

(57) ABSTRACT

Provided is a chromatography column stored in a storage container. The storage container for the column includes: a container body for storing the chromatography column; and a cover threadedly engaging with the container body. A groove for threaded engagement with the cover is formed in an inner wall of the container body. Sealing members are arranged on an inner bottom surface of the container body and a lower surface of the cover, respectively. When the container body and the cover are threadedly engaged with each other, the cover enters the container body to cause the sealing members on the inner bottom surface of the container body and the lower surface of the cover to press both a lower surface and an upper surface of the column, to
(Continued)

thereby fix the column inside the container body and seal a fluid passage hole of the column.

20 Claims, 5 Drawing Sheets

(51) Int. Cl.
  *G01N 30/60* (2006.01)
  *B65D 41/04* (2006.01)
  *B65D 53/02* (2006.01)
(58) Field of Classification Search
  USPC .......................................................... 73/431
  See application file for complete search history.

(56) References Cited

U.S. PATENT DOCUMENTS

| | | | |
|---|---|---|---|
| 5,407,568 | A | 4/1995 | Miura et al. |
| 8,197,694 | B1 | 6/2012 | Jin et al. |
| 9,168,492 | B2 * | 10/2015 | Bischoff ................ B01D 15/22 |
| 2006/0008390 | A1 | 1/2006 | Prentice et al. |
| 2007/0175809 | A1 | 8/2007 | Cao et al. |
| 2009/0230045 | A1 * | 9/2009 | Kaneko .................. B01J 20/283 |
| | | | 210/198.2 |
| 2016/0103103 | A1 * | 4/2016 | Yotani ................ G01N 30/6026 |
| | | | 73/61.53 |

FOREIGN PATENT DOCUMENTS

| | | | | |
|---|---|---|---|---|
| CN | 101180113 | A | | 5/2008 |
| CN | 201882145 | U | | 6/2011 |
| CN | 202389710 | U | | 8/2012 |
| CN | 203342439 | U | * | 12/2013 |
| DE | 18 17 999 | A1 | | 2/1977 |
| EP | 2 975 398 | A1 | | 1/2016 |
| GB | 2117074 | B | | 5/1985 |
| GB | 2212738 | | | 8/1989 |
| GB | 2212738 | A | * | 8/1989 ......... G01N 30/6069 |
| JP | 63 25366 | | | 2/1988 |
| JP | 6 94695 | | | 4/1994 |
| JP | 6 300747 | | | 10/1994 |
| JP | 2000 88829 | | | 3/2000 |
| JP | 2012 206758 | | | 10/2012 |
| JP | 2013 47880 | | | 3/2013 |
| WO | WO 02/04087 | A1 | | 1/2002 |
| WO | 2014 142096 | A1 | | 9/2014 |

OTHER PUBLICATIONS

Combined Office Action and Search Report issued Oct. 31, 2016 in Chinese Patent Application No. 201480053521.1 (with English translation of category of cited Documents).
Extended European Search Report issued Apr. 7, 2017, in European Patent Application No. 14849999.9.

* cited by examiner

COLUMN CONTAINED IN CONTAINER AND COLUMN CONTAINER

TECHNICAL FIELD

The present invention relates to a chromatography column stored contained in a storage container, and a storage container for a chromatography column.

BACKGROUND ART

A separation analysis method for a sample, such as chromatography, has been widely used for analysis and examination in fields such as organic chemistry, biochemistry, and medicine. A column to be used for chromatography is precisely prepared in accordance with an application thereof and a target substance, and utmost attention is required to be paid for transporting, handling, and storing the column.

It is necessary that a chromatography column be stored in a sealed manner in order to prevent contamination and drying of a filler therein when not in use. In a case where a threaded groove for fluid connection with an analysis device is formed in an inner wall of a fluid passage hole of the column, the column can be sealed by inserting a plug (such as a sealing plug, a stop plug, or a screw plug) into the fluid passage hole. In Patent Literature 1, there is a disclosure of a screw-type plug made of polytetrafluoroethylene (PTFE) for sealing a chromatography column when not in use. In the meantime, as disclosed in Patent Literature 2, there is also a column having no threaded groove. Further, when the column sealed with the plug is given shock by being dropped, a screw head may be broken to leave only a body of screw in the column, with the result that the column may not be used again. Further, when the column is given shock, the arrangement of the filler therein is disturbed, which hinders accurate measurement. Therefore, the conventional column has been generally stored by being sealed with a plug or the like and further being filled into a container together with a buffer.

CITATION LIST

Patent Literature

[PTL 1] JP-U-63-25366
[PTL 2] JP-A-2013-047880

SUMMARY OF INVENTION

Technical Problem

It is an object of the present invention to provide a column storage container, which is capable of storing a chromatography column in a safe and clean state and starting being used easily.

Solution to Problem

That is, the present invention provides a chromatography column stored in a storage container,
the storage container comprising:
a container body storing the chromatography column; and
a cover threadedly engaging with the container body,
wherein the container body has a groove, which is formed in an inner wall thereof, for a threaded engagement of the container body and the cover,
wherein the storage container further comprises sealing members arranged on an inner bottom surface of the container body and a lower surface of the cover, respectively, and
wherein, when the container body and the cover are threadedly engaged with each other, the cover enters the container body cause the sealing members on the inner bottom surface of the container body and the lower surface of the cover to press both a lower surface and an upper surface of the chromatography column, to thereby fix the chromatography column inside the container body and seal a fluid passage hole of the chromatography column.

Further, the present invention provides a storage container for a chromatography column, comprising:
a container body for storing the chromatography column; and
a cover threadedly engaging with the container body;
wherein the container body has a groove, which is formed in an inner wall thereof, for a threaded engagement of the container body and the cover,
wherein the storage container further comprises sealing members arranged on an inner bottom surface of the container body and a lower surface of the cover, respectively, and
wherein, when the container body and the cover are threadedly engaged with each other, the cover enters the container body to cause the sealing members on the inner bottom surface of the container body and the lower surface of the cover to press both a lower surface and an upper surface of the chromatography column, to thereby fix the chromatography column inside the container body and seal a fluid passage hole of the chromatography column.

Further, the present invention provides use of a storage container for storing a chromatography column,
the storage container comprising:
a container body for storing the chromatography column; and
a cover threadedly engaging with the container body,
wherein the container body has a groove, which is formed in an inner wall thereof, for a threaded engagement of the container body and the cover,
wherein the storage container further comprises sealing members arranged on an inner bottom surface of the container body and a lower surface of the cover, respectively, and
wherein, when the container body and the cover are threadedly engaged with each other, the cover enters the container body to cause the sealing members on the inner bottom surface of the container body and the lower surface of the cover to press both a lower surface and an upper surface of the chromatography column, to thereby fix the chromatography column inside the container body and seal a fluid passage hole of the chromatography column.

Further, the present invention provides a method of storing a chromatography column inside a storage container,
the storage container comprising:
a container body for storing the chromatography column; and
a cover threadedly engaging with the container body,
the container body having a groove, which is formed in an inner wall thereof, for a threaded engagement of the container body and the cover, the storage container further comprising sealing members arranged on an inner bottom surface of the container body and a lower surface of the cover, respectively, the method comprising:

storing the chromatography column into the container body; and threadedly engaging the container body storing the chromatography column and the cover with each other, (in which, through the threaded engaging, the cover enters the container body to cause the sealing members on the inner bottom surface of the container body and the lower surface of the cover to press both a lower surface and an upper surface of the chromatography column, to thereby fix the chromatography column inside the container body and seal a fluid passage hole of the chromatography column).

Advantageous Effects of Invention

The storage container for a chromatography column of the present invention may transport and store the chromatography column in a safe and clean state while protecting the chromatography column from shock and contamination. Further, the chromatography column stored in the storage container of the present invention may be easily taken out of the storage container and set in a device. Therefore, there are advantages in that operability is improved while risks of breakage and contamination are reduced.

BRIEF DESCRIPTION OF DRAWINGS

FIG. 6(a) is a side view thereof. FIG. 6(b) is a top view thereof. FIG. 6(c) is a bottom view thereof. FIG. 6(d) is a conceptual diagram for illustrating a state of the chromatography column stored in the column storage container illustrated in FIG. 1.

DESCRIPTION OF EMBODIMENTS

The present invention provides a storage container for storing a chromatography column, preferably, a liquid chromatography column such as a high-performance liquid chromatography (HPLC) column. There is no particular limitation on the size and shape of the chromatography column to be stored in the storage container of the present invention, and it is preferred that an external appearance of the chromatography column have a full length of from about 20 mm to about 80 mm and an outer diameter of from about 8 mm to about 12 mm from the viewpoint of a structure of the container of the present invention described later. Further, it is preferred that a fluid passage hole have a diameter of from about 0.1 mm to about 1.5 mm. Further, it is advantageous that an upper surface and a lower surface of the column are each a flat surface because the column can be supported stably in the container of the present invention. The storage container of the present invention is applicable to any of a column having a threaded groove on an inner wall of the fluid passage hole and a column having no threaded groove.

The storage container of the present invention comprises: a container body for storing the chromatography column; and a cover threadedly engaging with the container body. A groove for threaded engagement threadedly engaging with the cover is formed in an inner wall of the container body. Further, a groove for threaded engagement, which is to be paired with the groove for threaded engagement of the container body and threadedly engages with an inner wall of the container body, is formed on a side surface of the cover. Thus, when the container body and the cover are threadedly engaged with each other, the cover enters the container body.

The container body of the storage container of the present invention has such a size and a shape that the container body can store the chromatography column, and when the chromatography column is stored in the container, the chromatography column is allowed to stand by itself without tilting with respect to a center axis of the container body or falling down in the container by causing the container body having the column therein to stand upright. There is no particular limitation on the shape of an outer bottom surface of the container body, and the shape of the outer bottom surface of the container body is preferably such a shape as to enable the storage container to stand. Examples of the shape of the container body include a cylindrical shape, a polygonal column shape such as a hexagonal column shape or an octagonal column shape, or a tubular shape having a combination of the above-mentioned shapes (for example, a container body having an upper portion in a cylindrical shape and a lower portion in a polygonal column shape or a container body having an upper portion in a polygonal column shape and a lower portion in a cylindrical shape). Further, the function of preventing the container from rolling when the container falls down sideways can be further obtained by forming a part of the container body or an outer shape of the cover into a polygonal column shape. The minimum inner diameter of the container body is set to from about 101% to about 125%, preferably from about 101% to 115% of the outer diameter of the chromatography column to be stored.

The cover of the storage container of the present invention may have a shape different from an outer shape of the container body as long as the cover has a threaded engagement portion having a groove for threaded engagement that can threadedly engage with the inner wall of the container body. For example, in the storage container of the present invention, the container body may have a cylindrical shape, and the cover may have a polygonal column shape such as a hexagonal column shape or an octagonal column shape. Alternatively, in the storage container of the present invention, the upper portion of the container body may have a cylindrical shape, and the lower portion of the container body and the cover may each have a polygonal column shape such as a hexagonal column shape or an octagonal column shape.

Preferably, a non-slip portion may be formed on each of the container body and the cover. By virtue of the non-slip portion, when the container body and the cover are threadedly engaged with each other or the threaded engagement is released, the container body and the cover can be held easily, and the storage container of the present invention can be opened or closed easily. The non-slip portion may be a groove, a protrusion, a large number of irregularities, or a surface made of a material having high friction, which is formed in at least a part of an outer surface of each of the container body and the cover. Further, it is preferred that an inner bottom surface of the container body and a lower surface of the cover be substantially flat surfaces because the column can be supported more stably in the container of the present invention.

A sealing member is arranged on each of the inner bottom surface of the container body and a lower surface of the cover of the storage container of the present invention. The sealing member is formed of a material having high friction and elasticity, for example, an elastomer, such as an olefin-based elastomer or a styrene-based elastomer, a synthetic rubber, such as a fluoro-rubber, a nitrile rubber, a silicone rubber, a urethane rubber, or an ethylene propylene rubber, or a natural rubber. In one embodiment, the sealing member has a flat plate shape larger than the fluid passage hole of the column. In another embodiment, the sealing member has an O-ring shape having an outer diameter larger than that of the fluid passage hole but smaller than that of the upper surface or the lower surface of the column. In still another embodiment, one of the sealing members has the above-mentioned flat plate shape, and the other has the above-mentioned O-ring shape. Further, the shape of the sealing member is not limited to the above-mentioned embodiments as long as the sealing member can seal the fluid passage hole of the column, and any other shapes may be used. In any case, the sealing member is arranged in each center on the inner bottom surface of the container body and the lower surface of the cover, and when the cover of the container of the present invention is closed as described later, the sealing member can be brought into close contact with at least a periphery of the fluid passage hole on each of the upper surface and the lower surface of the column.

The sealing member serves to seal the fluid passage hole of the chromatography column stored in the storage container of the present invention, and to fix the column inside the storage container of the present invention. When the cover is closed in a state in which the chromatography column is stored in the container body of the storage container of the present invention, the cover is screwed into the container body, and hence the stored chromatography column is put into a state sandwiched between the inner bottom surface of the container body and the lower surface of the cover. In this case, two sealing members arranged on the inner bottom surface of the container body and the lower surface of the cover are each brought into close contact with at least the periphery of the fluid passage hole of the column on any of the upper surface and the lower surface of the column, to thereby seal the fluid passage hole. When the sealing member has, for example, a flat plate shape, through closing of the cover of the container, the fluid passage hole on the upper surface or the lower surface of the column is covered to be sealed with the sealing member. Further, when the sealing member has, for example, an O-ring shape, through closing of the cover of the container, the sealing member is brought Into close contact with the periphery of the fluid passage hole of the upper surface or the lower surface of the column to surround the fluid passage hole together with the bottom surface of the container body or the lower surface of the cover, thereby being capable of sealing the fluid passage hole. Further, the two sealing members fix the column inside the container body by pressing the column from both the upper surface and the lower surface thereof.

The sealing member formed of an elastic material further can serve to absorb shock from outside to the chromatography column stored in the storage container of the present invention. Thus, it is desired that the sealing member be thicker from the viewpoint of shock absorption. However, considering the economic viewpoint, the thickness of the sealing member is preferably from about 0.3 mm to 3.0 mm. In the case where the shock absorption of the sealing member is not sufficient for transportation or storage environment, the shock resistance can be enhanced more by covering the chromatography column stored in the storage container further with a buffer or the like.

The container body and the cover of the storage container of the present invention each may be formed of a general-purpose resin, such as polymethyl methacrylate (PMMA), polypropylene (PP), polyethylene (PE) polycarbonate (PC) acrylonitrile-butadiene-styrene copolymer (ABS). It is preferred that at least a part of a side wall or an entire side wall of the container body be formed of a transparent or semi-transparent material so that the column stored in the storage container can be visually recognized. More preferably, the container body and the cover are formed of a transparent or semi-transparent material. Preferably, the storage container of the present invention is a self-standing type and can hold the stored column upright.

The chromatography column stored in the storage container of the present invention is sealed and stably fixed inside the container with the cover through the sealing members having high friction and elasticity, and hence the chromatography column is protected from shock and contamination. Further, even when the cover of the storage container is opened, the column does not tilt or fall down in the container and is easily released from a fixed state, and the sealing can also be removed. Thus, the chromatography column of the present invention can be easily taken out of the container with a minimum operation without any risk of breakage and contamination, and can be set in a device.

In addition to the above, according to the present invention, the use of the storage container of the present invention for storing the chromatography column is provided. There is also provided a method of storing the chromatography column through use of the storage container of the present invention. The details of the use and storage method are as described above.

EXAMPLES

Hereinafter, embodiments of the present invention are further described in detail with reference to the drawings. Embodiments of the present invention illustrated in the drawings are merely examples of the present invention, and the present invention is not limited to those embodiments. Needless to say, in addition to the matters directly described in the embodiments, the present invention encompasses various improvements and modifications that may be made by a person skilled in the art within the scope of claims.

Figure 1:
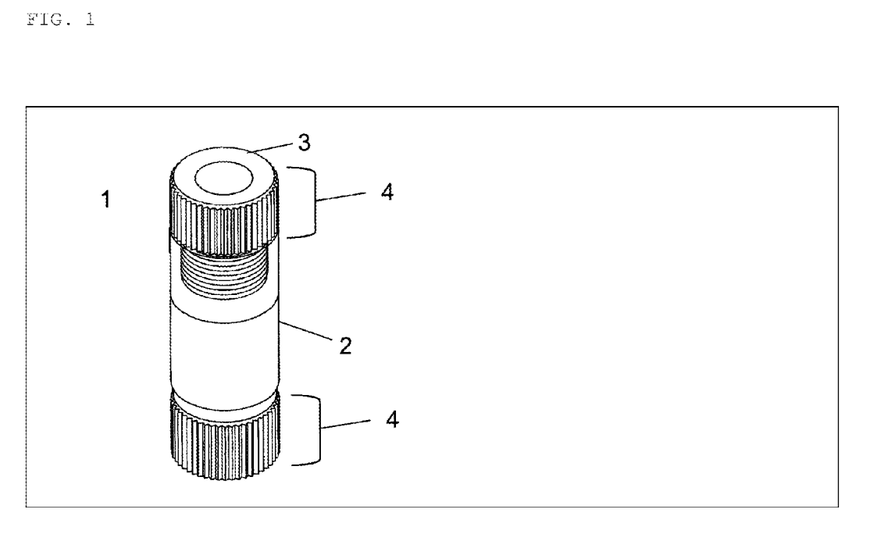
FIG. 1 is an illustration of an example of a column storage container of the present invention.
Figure 2:
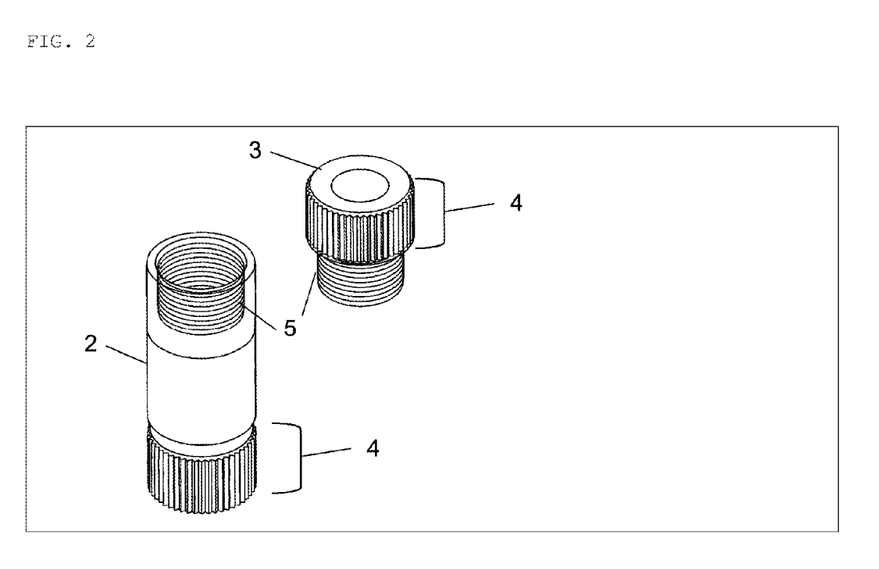
FIG. 2 is an illustration of the column storage container illustrated in FIG. 1 in a state in which a cover is removed from a container body.

FIG. 1 is a perspective view of an example of a column storage container of the present invention. A column storage container 1 according to this embodiment is a cylindrical self-standing container having a side wall formed of a transparent material, and a container body and a cover are threadedly engaged with each other. A cover 3 threadedly engaged with a container body 2 is placed inside the container body 2. As a non-slip portion during opening/closing of the container, a non-slip groove 4 is formed in each of outer surfaces of the cover 3 and a lower portion of the container body 2. FIG. 2 is an illustration of a state in which the cover 3 is removed from the container body 2 in the column storage container 1 illustrated in FIG. 1. Groove for threaded engagements 5 to be paired are formed in an inner wall of the container body 2 and a side surface of the cover 3.

Figure 3:
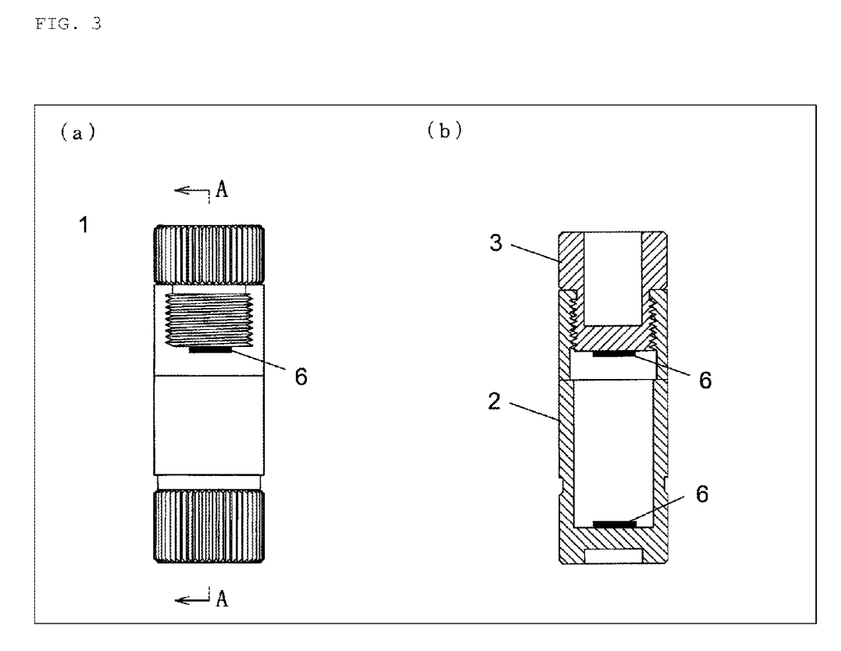
FIG. 3(a) is a side view of the column storage container illustrated in FIG. 1.
FIG. 3(b) is a sectional view taken along the line A-A of FIG. 3(a).

FIG. 3 are a side view (FIG. 3a) of the column storage container 1 illustrated in FIG. 1 and a sectional view (FIG. 3b) thereof. As illustrated in FIG. 3b, both an inner bottom surface of the container body 2 and a lower surface of the cover 3 are a flat surface, and a sealing member 6 is arranged on each of the inner bottom surface of the container body 2 and the lower surface of the cover 3. In this embodiment, the sealing member 6 is formed of a fluoro-rubber, and has a diameter larger than that of a fluid passage hole and a thickness of 1.5 mm.

Figure 4:
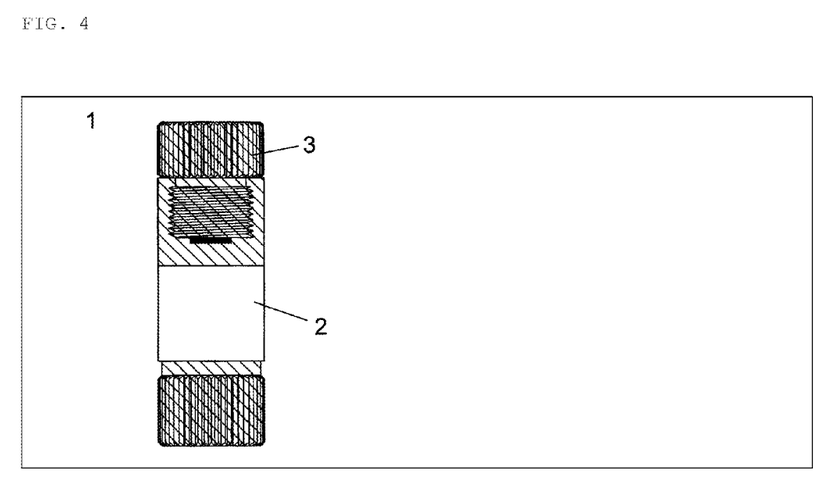
FIG. 4 is an illustration of an example of the column storage container of the present invention, in which only a part of a side wall of the container body is formed of a transparent material.

FIG. 4 is an illustration of an example of the column storage container 1 of the present invention, in which only a center of the side wall of the container body 2 is formed of a transparent material, and the others (shaded portions) are formed of a semi-transparent material.

Figure 5:
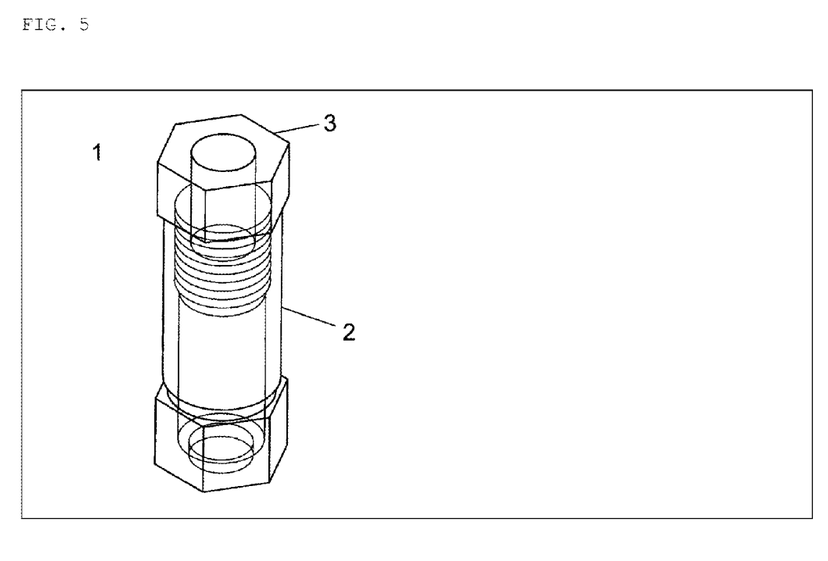
FIG. 5 is an illustration of another example of the column storage container of the present invention.

FIG. 5 is a perspective view of another example of the column storage container according to the present invention. In this embodiment, the shape of the container body 2 is a combination of a cylindrical shape and a hexagonal column shape, and the cover 3 includes a head having a hexagonal column shape and a threaded engagement portion having a groove for threaded engagement.

Figure 6:
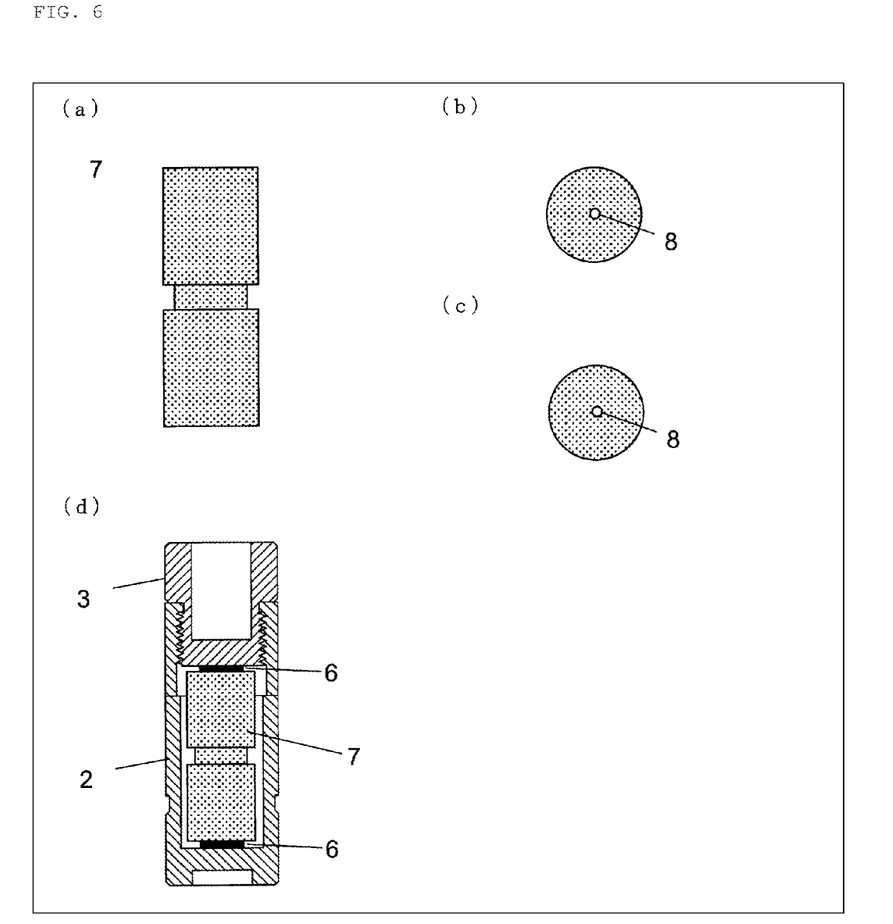
FIG. 6 are each an illustration of an example of a chromatography column to be stored in the column storage container of the present invention.

FIG. 6a to FIG. 6c are a side view (a), a top view (b), and a bottom view (c) of an example of a chromatography column 7 to be stored in the column storage container of the present invention. The column 7 has a columnar shape, and an upper surface and a lower surface thereof are flat surfaces, each having a fluid passage hole 8. FIG. 6d is a conceptual diagram for illustrating a state of the chromatography column 7 stored in the column storage container 1 illustrated in FIG. 1. The upper surface and the lower surface of the column 7 are respectively held in close contact with the sealing members 6 arranged on the lower surface of the cover 3 and the inner bottom surface of the container body 2. The column 7 is pressed from above and below through the two sealing members 6. With such press, the column 7 is fixed inside the storage container 1, and the fluid passage holes S formed in the upper surface and the lower surface of the column 7 are sealed with the sealing members 6.

Figure 7:
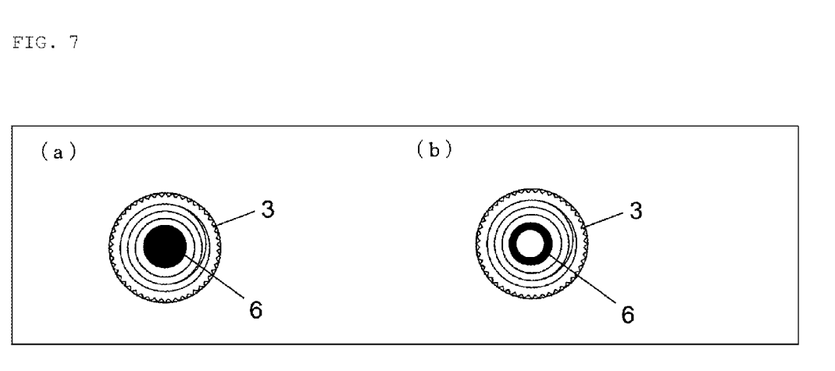
FIG. 7 are each a bottom view of a cover 3 of the column storage container 1 illustrated in FIG. 1.

FIG. 7 are each a bottom view of the cover 3 of the column storage container 1 of FIG. 1, and the sealing member 6 is illustrated therein. In FIG. 7a, the sealing member 6 has a disc shape having a diameter larger than that of the fluid passage hole and can cover and seal the fluid passage hole 8. In FIG. 7b, the sealing member 6 has an O-ring shape having an outer diameter larger than that of the fluid passage hole and can seal the fluid passage hole 8 by surrounding a periphery of the fluid passage hole 8.

REFERENCE SIGNS LIST 1 column storage container
2 container body
3 cover
4 non-slip groove
5 groove for threaded engagement
6 sealing member
7 chromatography column
8 fluid passage hole

The invention claimed is:

1. An article, comprising:
   a storage container comprising a container body, a cover threadedly engagable with the container body, and sealing members positioned on an inner bottom surface of the container body and a lower surface of the cover, respectively; and
   a chromatography column having fluid passage holes on a lower surface and an upper surface, respectively, and configured to be stored in the container body of the storage container,
   wherein
   the container body has a groove formed in an inner wall of the container body and configured to threadedly engage the container body and the cover such that
   at least a part of the cover enters the container body, that the sealing member on the inner bottom surface of the container body presses the lower surface of the chromatography column and the sealing member on the lower surface of the cover presses the upper surface of the chromatography column to fix the chromatography column inside the container body, and that the fluid passage holes of the chromatography column are sealed.

2. The article of claim 1, wherein the container body has a tubular shape having a minimum inner diameter of from 101% to 125% of an outer diameter of the chromatography column.

3. The article of claim 1, wherein each of the sealing members comprises a flat plate or an O-ring formed of a material having high friction and elasticity.

4. The article of claim 1, wherein the storage container is self-standable.

5. A storage container, comprising:
   a container body configured to store a chromatography column therein;
   a cover threadedly engagable with the container body; and
   sealing members positioned on an inner bottom surface of the container body and a lower surface of the cover, respectively,
   wherein
   the container body has a groove formed in an inner wall of the container body and configured to threadedly engage the container body and the cover such that
   at least a part of the cover enters the container body, that the sealing member on the inner bottom surface of the container body presses a lower surface of the chromatography column and the sealing member on the lower surface of the cover presses an upper surface of the chromatography column to fix the chromatography column inside the container body, and that fluid passage holes of the chromatography column formed on respective one of the lower surface and the upper surface of the chromatography column are sealed.

6. The storage container of claim 5, wherein the container body has a tubular shape having a minimum inner diameter of from 101% to 125% of an outer diameter of the chromatography column.

7. The storage container of claim 5, wherein each of the sealing members comprises a flat plate or an O-ring formed of a material having high friction and elasticity.

8. The storage container of claim 5, wherein the storage container is self-standable.

9. The article of claim 1, wherein the sealing members comprise a flat plate, and the groove of the container is configured to threadedly engage the container body and the cover such that the fluid passage holes of chromatography column are sealed by the flat plate.

10. The article of claim 1, wherein the sealing members comprise an O-ring, and the groove of the container is configured to threadedly engage the container body and the cover such that the fluid passage holes of chromatography column are sealed by the O-ring and one of the bottom surface of the container body and the lower surface of the cover.

11. The article of claim 1, wherein the sealing members have a thickness of from about 0.3 mm to 3.0 mm.

12. The article of claim 1, wherein at least a part of the container body or the cover is in a polygonal column shape.

13. The article of claim 1, wherein the sealing members comprise at least one of an elastomer, a synthetic rubber, and a natural rubber.

14. The article of claim 1, wherein each of the sealing members comprises a flat plate having a diameter larger than a diameter of the fluid passage holes of the chromatography column, or an O-ring having an outer diameter larger than the diameter of the fluid passage holes of the chromatography column.

15. The storage container of claim 5, wherein the sealing members comprise a flat plate, and the groove of the container is configured to threadedly engage the container body and the cover such that the fluid passage holes of chromatography column are sealed by the flat plate.

16. The storage container of claim 5, wherein the sealing members comprise an O-ring, and the groove of the container is configured to threadedly engage the container body and the cover such that the fluid passage holes of chromatography column are sealed by the O-ring and one of the bottom surface of the container body and the lower surface of the cover.

17. The storage container of claim 5, wherein the sealing members have a thickness of from about 0.3 mm to 3.0 mm.

18. The storage container of claim 5, wherein at least a part of the container body or the cover is in a polygonal column shape.

19. The storage container of claim 5, wherein the sealing members comprise at least one of an elastomer, a synthetic rubber, and a natural rubber.

20. The storage container of claim 5, wherein each of the sealing members comprises a flat plate having a diameter larger than a diameter of the fluid passage holes of the chromatography column, or an O-ring having an outer diameter larger than the diameter of the fluid passage holes of the chromatography column.

* * * * *